(12) United States Patent
Johnson et al.

(10) Patent No.: US 6,723,102 B2
(45) Date of Patent: *Apr. 20, 2004

(54) APPARATUS AND METHOD FOR MINIMALLY INVASIVE TOTAL JOINT REPLACEMENT

(75) Inventors: Wesley D. Johnson, Eden Prairie, MN (US); Gerard Engh, Alexandria, VA (US)

(73) Assignee: Alexandria Research Technologies, LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/075,829

(22) Filed: Feb. 12, 2002

(65) Prior Publication Data

US 2002/0193797 A1 Dec. 19, 2002

Related U.S. Application Data

(63) Continuation-in-part of application No. 09/882,591, filed on Jun. 14, 2001.
(60) Provisional application No. 60/331,930, filed on Nov. 21, 2001.

(51) Int. Cl.$^7$ .............................................. A61B 17/32
(52) U.S. Cl. ............................ 606/79; 606/80; 606/86; 606/88; 623/20.21
(58) Field of Search .......................... 606/79, 80, 88, 606/86, 170, 180, 176, 177, 179; 623/20.21, 20.32, 20.31, 20.35, 20.14, 20.15

(56) References Cited

U.S. PATENT DOCUMENTS

| | | | |
|---|---|---|---|
| 3,953,899 A | 5/1976 | Charnley ..................... | 3/1.911 |
| 3,958,278 A | 5/1976 | Lee et al. .................... | 3/1.911 |
| 4,085,466 A | 4/1978 | Goodfellow et al. ........... | 3/1.91 |
| 4,340,978 A | 7/1982 | Buechel et al. .............. | 3/1.911 |
| 4,457,307 A | 7/1984 | Stillwell ..................... | 128/317 |
| 4,487,203 A | 12/1984 | Androphy .................... | 128/303 |
| 4,524,766 A | 6/1985 | Petersen ....................... | 128/92 |
| 4,567,885 A | 2/1986 | Androphy ..................... | 128/92 |
| 4,574,794 A | 3/1986 | Cooke et al. ................. | 128/92 |
| 4,662,891 A | * 5/1987 | Noiles ..................... | 623/22.31 |
| 4,714,474 A | 12/1987 | Brooks, Jr. et al. ........... | 623/20 |
| 4,759,350 A | 7/1988 | Dunn et al. .................... | 128/92 |
| 4,838,891 A | 6/1989 | Branemark et al. ........... | 623/20 |
| 4,938,762 A | 7/1990 | Wehrli ......................... | 606/88 |
| 4,944,760 A | 7/1990 | Kenna .......................... | 623/20 |

(List continued on next page.)

FOREIGN PATENT DOCUMENTS

| | | | |
|---|---|---|---|
| DE | 19 64 781 | 12/1969 | |
| DE | 21 20 320 | 11/1972 | |
| DE | 28 30 566 A1 | 7/1978 | ............. A61F/1/00 |
| DE | 296 09 632 U1 | 12/1996 | ............. A61F/2/46 |
| DE | 200 21 494 U1 | 5/2001 | ............ A61B/17/17 |
| EP | 0 647 432 A1 | 10/1993 | ............ A61B/17/14 |
| EP | 0 685 210 A1 | 5/1995 | ............. A61F/2/38 |
| EP | 0 709 061 A1 | 5/1996 | ............ A61B/17/15 |
| EP | 0 720 834 A3 | 7/1996 | ............ A61B/17/02 |
| EP | 0 720 834 A2 | 7/1996 | ............ A61B/17/02 |

(List continued on next page.)

Primary Examiner—Pedro Philogene

(57) ABSTRACT

A method and apparatus for minimally invasive total joint replacement. The method involves sculpting the articular surface of a second bone that normally articulates with a first bone by attaching a bone sculpting tool directly or indirectly to the first bone with the tool in bone sculpting engagement with the articular surface of the second bone, and then sculpting the articular surface of the second bone with the joint reduced and moving one bone with respect to the other. An implant is placed to replace the articular surface of the second bone using an impaction device directly or indirectly attached to the first bone, wherein the force to place the implant is reacted by the second bone and the first bone.

59 Claims, 11 Drawing Sheets

U.S. PATENT DOCUMENTS

| | | |
|---|---|---|
| 5,030,221 A | 7/1991 | Buechel et al. ............... 606/91 |
| 5,037,423 A | 8/1991 | Kenna .......................... 606/88 |
| 5,047,032 A | 9/1991 | Jellicoe ........................ 606/83 |
| 5,108,448 A * | 4/1992 | Gautier .................... 623/22.26 |
| D331,461 S | 12/1992 | Lester ........................ D24/140 |
| D337,639 S | 7/1993 | Beckman ................... D24/133 |
| 5,234,433 A | 8/1993 | Bert et al. ..................... 606/86 |
| 5,250,050 A | 10/1993 | Poggie et al. ................. 606/79 |
| 5,263,498 A | 11/1993 | Caspari et al. .............. 128/898 |
| 5,331,975 A | 7/1994 | Bonutti ...................... 128/898 |
| 5,417,693 A | 5/1995 | Sowden et al. .............. 606/85 |
| 5,417,695 A | 5/1995 | Axelson, Jr. .................. 606/89 |
| 5,423,822 A | 6/1995 | Hershberger et al. ......... 606/79 |
| 5,474,560 A | 12/1995 | Rohr, Jr. ....................... 606/91 |
| 5,486,178 A | 1/1996 | Hodge ......................... 606/82 |
| 5,540,696 A | 7/1996 | Booth, Jr. et al. ............. 606/88 |
| 5,569,255 A | 10/1996 | Burke .......................... 606/79 |
| 5,575,793 A | 11/1996 | Carls et al. ................... 606/80 |
| 5,578,039 A | 11/1996 | Vendrely et al. .............. 606/88 |
| 5,609,642 A | 3/1997 | Johnson et al. ............... 623/20 |
| 5,624,443 A | 4/1997 | Burke .......................... 606/86 |
| 5,658,292 A | 8/1997 | Axelson, Jr. .................. 606/86 |
| 5,667,511 A | 9/1997 | Vendrely et al. .............. 606/88 |
| 5,669,914 A | 9/1997 | Eckhoff ....................... 606/88 |
| 5,683,469 A | 11/1997 | Johnson et al. ............... 623/20 |
| 5,683,470 A | 11/1997 | Johnson et al. ............... 623/20 |
| 5,688,280 A | 11/1997 | Booth, Jr. et al. ............. 606/88 |
| 5,690,636 A | 11/1997 | Wildgoose et al. ............ 606/88 |
| 5,690,638 A | 11/1997 | Dance et al. ................. 606/88 |
| 5,693,056 A | 12/1997 | Carls et al. ................... 606/86 |
| 5,716,360 A | 2/1998 | Baldwin et al. .............. 606/80 |
| 5,725,596 A | 3/1998 | Burke .......................... 623/23 |
| 5,741,264 A | 4/1998 | Cipolletti ..................... 606/85 |
| 5,769,854 A | 6/1998 | Bastian et al. ................ 606/88 |
| 5,776,200 A | 7/1998 | Johnson et al. ............... 623/20 |
| 5,788,701 A | 8/1998 | McCue ........................ 606/88 |
| 5,795,353 A | 8/1998 | Felt .............................. 623/18 |
| 5,800,438 A | 9/1998 | Tuke et al. .................... 606/90 |
| 5,810,830 A | 9/1998 | Noble et al. .................. 606/85 |
| 5,824,098 A | 10/1998 | Stein ........................... 623/20 |
| 5,824,104 A | 10/1998 | Tuke ........................... 623/20 |
| 5,827,290 A * | 10/1998 | Bradley ....................... 606/86 |
| 5,830,216 A | 11/1998 | Insall et al. ................... 606/88 |
| 5,851,183 A | 12/1998 | Bucholz ..................... 600/425 |
| 5,880,976 A | 3/1999 | DiGioia III et al. ........ 364/578 |
| 5,885,299 A | 3/1999 | Winslow et al. .............. 606/99 |
| 5,891,034 A | 4/1999 | Bucholz ..................... 600/426 |
| 5,897,559 A * | 4/1999 | Masini ......................... 606/86 |
| 5,925,049 A | 7/1999 | Gustilo et al. ................ 606/82 |
| 5,951,564 A | 9/1999 | Schroder et al. ............ 606/100 |
| 5,951,606 A | 9/1999 | Burke .......................... 623/23 |
| 5,976,147 A | 11/1999 | LaSalle et al. ................ 606/88 |
| 5,976,148 A * | 11/1999 | Charpenet et al. ............ 606/91 |
| 5,989,261 A | 11/1999 | Walker et al. .............. 606/102 |
| 5,997,543 A | 12/1999 | Truscott ....................... 606/86 |
| 6,002,859 A | 12/1999 | DiGioia, III et al. ... 395/500.32 |
| 6,010,509 A | 1/2000 | Delgado et al. .............. 606/88 |
| 6,013,081 A | 1/2000 | Burkinshaw et al. ......... 606/88 |
| 6,018,094 A | 1/2000 | Fox .............................. 623/11 |
| 6,056,756 A | 5/2000 | Eng et al. ..................... 606/87 |
| 6,059,831 A | 5/2000 | Braslow et al. ............... 623/20 |
| 6,063,091 A | 5/2000 | Lombardo et al. ............ 606/88 |
| 6,090,114 A | 7/2000 | Matsuno et al. .............. 606/88 |
| 6,096,043 A | 8/2000 | Techiera et al. .............. 606/88 |
| 6,106,529 A | 8/2000 | Techiera ...................... 606/88 |
| 6,132,468 A | 10/2000 | Mansmann .............. 623/20.16 |
| 6,146,390 A | 11/2000 | Heilbrun et al. ............ 606/130 |
| 6,159,214 A | 12/2000 | Michelson ................... 606/80 |
| 6,165,181 A | 12/2000 | Heilbrun et al. ............ 606/130 |
| 6,179,877 B1 | 1/2001 | Burke ...................... 623/22.12 |
| 6,197,064 B1 | 3/2001 | Haines et al. ............ 623/20.31 |
| 6,201,984 B1 | 3/2001 | Funda et al. ................ 600/407 |
| 6,206,927 B1 | 3/2001 | Fell et al. ................ 623/20.29 |
| 6,231,611 B1 | 5/2001 | Mosseri .................... 623/22.12 |
| 6,236,875 B1 | 5/2001 | Bucholz et al. ............. 600/407 |
| RE37,277 E | 7/2001 | Baldwin et al. ............... 623/20 |
| 6,283,980 B1 | 9/2001 | Vibe-Hansen et al. ....... 606/151 |
| 6,290,704 B1 | 9/2001 | Burkinshaw et al. ......... 606/88 |
| 6,332,780 B1 | 12/2001 | Traxel et al. ................ 434/267 |
| 6,379,367 B1 | 4/2002 | Vibe-Hansen et al. ....... 606/151 |
| 6,482,209 B1 * | 11/2002 | Engh et al. ................... 606/79 |
| 2001/0012967 A1 | 8/2001 | Mosseri .................... 623/23.12 |

FOREIGN PATENT DOCUMENTS

| | | | | |
|---|---|---|---|---|
| EP | | 0 780 090 A1 | 6/1997 | ........... A61B/17/16 |
| EP | | 0780 092 A1 | 6/1997 | ........... A61B/17/56 |
| EP | | 0 824 904 A2 | 7/1997 | ............. A61F/2/46 |
| EP | | 0 842 639 A2 | 5/1998 | ........... A61B/17/17 |
| EP | | 0 824 904 A3 | 11/1998 | ............. A61F/2/46 |
| EP | | 1 099 430 A1 | 11/1999 | ............. A61F/2/46 |
| EP | | 1 086 668 A1 | 3/2001 | ............. A61F/2/46 |
| EP | | 1 084 680 A3 | 5/2001 | ........... A61B/17/14 |
| EP | | 1 149 562 A2 | 10/2001 | ........... A61B/17/17 |
| FR | | 2 266 492 | 10/1975 | ............. A61F/1/24 |
| FR | | 2 589 720 | 11/1985 | ............. A61F/2/38 |
| WO | | WO 99/59669 | 11/1999 | .......... A61M/29/00 |
| WO | | WO 01/66021 A1 | 9/2001 | ........... A61B/17/14 |
| WO | | WO 01/66022 A1 | 9/2001 | ........... A61B/17/14 |

* cited by examiner

APPARATUS AND METHOD FOR MINIMALLY INVASIVE TOTAL JOINT REPLACEMENT

This application is a continuation in part of Ser. No. 09/882,591, filed Jun. 18, 2001 and claims benafit of Provisional Appr. No. 60/331,930 filed Nov. 21, 2001.

BACKGROUND OF THE INVENTION

A joint generally consists of two relatively rigid bony structures that maintain a relationship with each other. Soft tissue structures spanning the bony structures hold the bony structures together and aid in defining the motion of one bony structure relative to the other. In the knee, for example, the bony structures are the tibia and the femur. Soft tissue such as ligaments, tendons, menisci, and capsule provide support to the tibia and femur. A smooth and resilient surface consisting of articular cartilage covers the bony structures. The articular surfaces of the bony structures work in concert with the soft tissue structures to form a mechanism that defines the envelop of motion between the structures. When fully articulated, the motion defines a total envelop of motion between the bony structures. Within a typical envelop of motion, the bony structures move in a predetermined pattern with respect to one another. In the example of the hip joint, the joint is a ball in socket joint that is inherently stable. The capsule and ligaments spanning the hip joint provide stability while the muscles provide motion.

The articular surfaces of the bony structure became damaged by a variety of diseases, accidents, and other causes. A common disorder of joints is degenerative arthritis. Degenerative arthritis causes progressive pain, swelling, and stiffness of the joints. As the arthritis progresses the joint surfaces wear away, resulting in contractures of the surrounding soft tissues that provide stability to the joint. Moreover, progression of the disease process increases pain and reduces mobility.

Treatment of the afflicted articular bone surfaces depends, among other things, upon the severity of the damage to the articular surface and the age and general physical robustness of the patient. Commonly, for advanced arthritis, joint replacement surgery is necessary wherein the articulating elements of the joint are replaced with artificial elements commonly consisting of a part made of metal articulating with a part made of ultra high molecular weight polyethylene (UHMWPE).

A relatively young patient with moderate to severe degeneration of the hip joint is often treated with drug therapies. While drug therapies may temporarily provide relief of pain, progression of the disease, with resulting deformity and reduced function, ultimately necessitates surgery. Alternative treatments such as non-steroidal anti-inflammatory drugs and cortisone injections similarly provide only temporary relief of symptoms.

In severe situations, the entire articular surface of a bone may be replaced with an artificial surface, as, for example, when the acetabular socket and femoral head are replaced with a prosthetic device including an UHMWPE bearing to resurface the acetabulum and a polished metal or ceramic femoral head mounted to a stem extending into the medullary canal of the proximal femur to replace the femoral head. Joint replacement surgery has become a proven and efficacious method of alleviating pain and restoring function of the joint.

Current methods of preparing the rigid elements of a joint to receive components as in joint replacement surgery involve extensive surgical exposure. The exposure must be sufficient to permit the introduction of drills, reamers, broaches and other instruments for cutting or removing cartilage and bone that subsequently is replaced with artificial surfaces. For total hip replacement, the acetabular articular surface and subchondral bone is removed by spherical reamers, the femoral head is resected with an oscillating saw, and the proximal medullary canal is shaped with broaches. A difficulty with total hip replacement is that the invasiveness of the procedure causes significant interoperative blood loss and extensive rehabilitation because muscles and tendons must be released from the proximal femur to mobilize the femur and gain exposure of and access to the acetabular fossa.

Invasiveness. Conventional total hip arthroplasty is indicated for painful arthritis of the hip joint. The procedure involves exposing the hip joint through a large incision to provide the surgeon full visualization of the hip joint and the acetabular region and to provide access for surgical power instruments. In order to appropriately prepare the bony structures of the hip joint, the major muscles spanning the joint are commonly disrupted to gain adequate exposure of the joint. Steps of the procedure include removing the femoral head followed by reaming and broaching the proximal femoral canal to prepare a bony surface to support a hip stem. The stem is implanted and may be cemented in place, or press fit for bony ingrowth. The acetabulum is typically prepared using a hemispherical reamer to remove cartilage down to bleeding bone. Once the acetabulum is prepared, an acetabular component is implanted, either by cementing in place or press fitting for bony ingrowth. Surgical exposure is necessary to accommodate the bulk and geometry of the components as well as the instruments for bone preparation. The surgical exposure, which may be between six and twelve inches in length, may result in extensive trauma to the soft tissues surrounding the hip joint along with the release of muscles that insert into the proximal femur. The surgical exposure increases bleeding, pain, and muscle inhibition; all of which contribute to a longer hospitalization and rehabilitation before the patient can be safely discharged to home or to an intermediate care facility.

The prepared bony surfaces are technically referred to as the acetabular fossa, femoral canal and metaphyseal region of the femur. Prior to placing the final implants into the prepared spaces, a femoral trial, which may be the broach in some systems, is placed in the proximal femur along with a trial femoral head and neck, and an acetabular trial is placed into the acetabulum to facilitate trial range of motion and evaluation of hip stability prior to placement of the final total hip implants.

For patients who require hip replacement it is desirable to provide surgical methods and apparatuses that may be employed to gain surgical access to articulating joint surfaces, to appropriately prepare the bony structures, to provide artificial, e.g., metal or plastic, articular bearing surfaces, and to close the surgical site, all without substantial damage or trauma to associated muscles, ligaments or tendons. To attain this goal, a system and method is needed to enable articulating surfaces of the joints to be appropriately sculpted using minimally invasive apparatuses and procedures.

A system to enable minimally invasive total hip arthroplasty that will minimize soft tissue trauma and accelerate postoperative rehabilitation is needed. Further, because minimally invasive techniques inherently limit observation of the surgical site, compromising visualization of the prepared bony surfaces, a device is also needed for inspection of the prepared bony surfaces. During a surgical procedure, bone debris and blood will gather in the surgical site and require removal from time to time to visualize the acetabulum. After preparation of the acetabulum, an acetabular component is implanted. A variety of acetabular components such as cemented UHMWPE cups, cemented or press fit metal shells with UHMWPE, metal, or ceramic bearing liners are presently used. Typically, placement of a press fit shell requires an impaction force to fully seat the implant into support bone. However, the size and location of the minimally invasive incision may not be optimal for proper orientation and application of force to adequately seat and stabilize an acetabular implant. Thus, an impaction device is needed that allows for impaction of the acetabular component with the hip reduced or articulated for use with a minimally invasive exposure for total hip arthroplasty. It may also be desirable to use a surgical navigation system to position the acetabular implant.

SUMMARY OF THE INVENTION

The present invention provides a system and method for total joint replacement that involves minimally invasive surgical procedures. The instruments disclosed accomplish accurate bone preparation, implant orientation and implant fixation through a limited surgical exposure.

Thus, in one embodiment, the present invention provides a method of appropriately sculpting the articular surface of a second bone that normally articulates with a first bone. The method involves attaching a bone sculpting tool directly or indirectly to the first bone with the tool in bone sculpting engagement with the articular surface of the second bone, and then sculpting the articular surface of the second bone with the joint reduced and moving one bone with respect to the other. Optionally, the bone sculpting tool may be attached to a mount that is attached directly or indirectly to the first bone. In some situations, it may be desirable to distract the second bone from the first bone during surgery.

In a further embodiment, the invention provides a method of appropriately preparing the articular surface of a second bone that normally articulates with a first bone and implanting a prosthetic device. The method involves attaching a bone sculpting tool directly or indirectly to the first bone with the tool in bone sculpting engagement with the articular surface of the second bone, and then sculpting the articular surface by articulating one of the bones with respect to the other while bone preparation is performed. The bone sculpting tool may be attached to a bone mount that is directly or indirectly attached to or integral with a stem, trial, reamer or broach implanted in the medullary canal of a bone.

Specifically, for example, the invention may be used for replacing the surfaces of a femur and acetabulum through a minimal incision and with minimal disruption of musculotendinous structures about the hip. A typical incision for a minimally invasive total hip procedure is between two and four inches in length. It is noted that there may be some variation in incision length due to patient physiology, surgeon preferences, and/or other factors; the stated range is illustrative, not limiting. In addition to a small incision, care is taken to approach the joint capsule by separating tissues between muscle groups, rather than sectioning specific muscles. The invention includes; in various embodiments:

1. A Minimally Invasive Acetabular Reamer System (MIAR)

The MIAR is either a modular or non-modular construct that, for hip applications, comprises a femoral trial, a drive mechanism (either integral or separate) and a hemispherical reamer or similar device for removing cartilage and bone from the acetabular fossa. The reaming system enables placement of the components through a small incision and minimizes the number of components in the instrument set.

2. A Device to Illuminate and Visualize the Acetabulum

A fiber optic system is provided including a light source, fiber optic cable, imaging base and an imaging device and monitoring system to ensure proper preparation of the acetabulum.

3. An Apparatus to Flush and Remove Bone Debris and Blood from the Surgical Site An irrigation system and a suction system are provided. The irrigation and suction systems may be integral to the imaging base, or separate instruments available for use as needed during the procedure.

4. A Minimally Invasive Acetabular Impaction System (MIAI)

An acetabular component, such as a press fit shell, is implanted following preparation of the acetabulum. An impaction device is provided that allows for impaction of the acetabular component with the hip reduced or articulated in order to fully seat a press fit acetabular component into support bone of the acetabulum. The MIAI may not be needed with some acetabular components. A surgical navigation system for positioning the acetabular component may be used with the MIAI.

In the minimally invasive procedure, the hip is accessed through an incision adequate to expose the trochanteric fossa and allow resection of the femoral neck and removal of the femoral head and neck segment. The femoral canal is accessed through the trochanteric fossa and trochanteric region. Reamers, rasps and other devices as are known to those skilled in the art are used to prepare the proximal femur to receive a femoral implant by a sequence of reaming and broaching steps. Once prepared, the intramedullary canal and retained area of the femoral neck and trochanteric region are used to support the MIAR system to prepare the acetabulum.

DETAILED DESCRIPTION OF THE INVENTION

Figure 1:
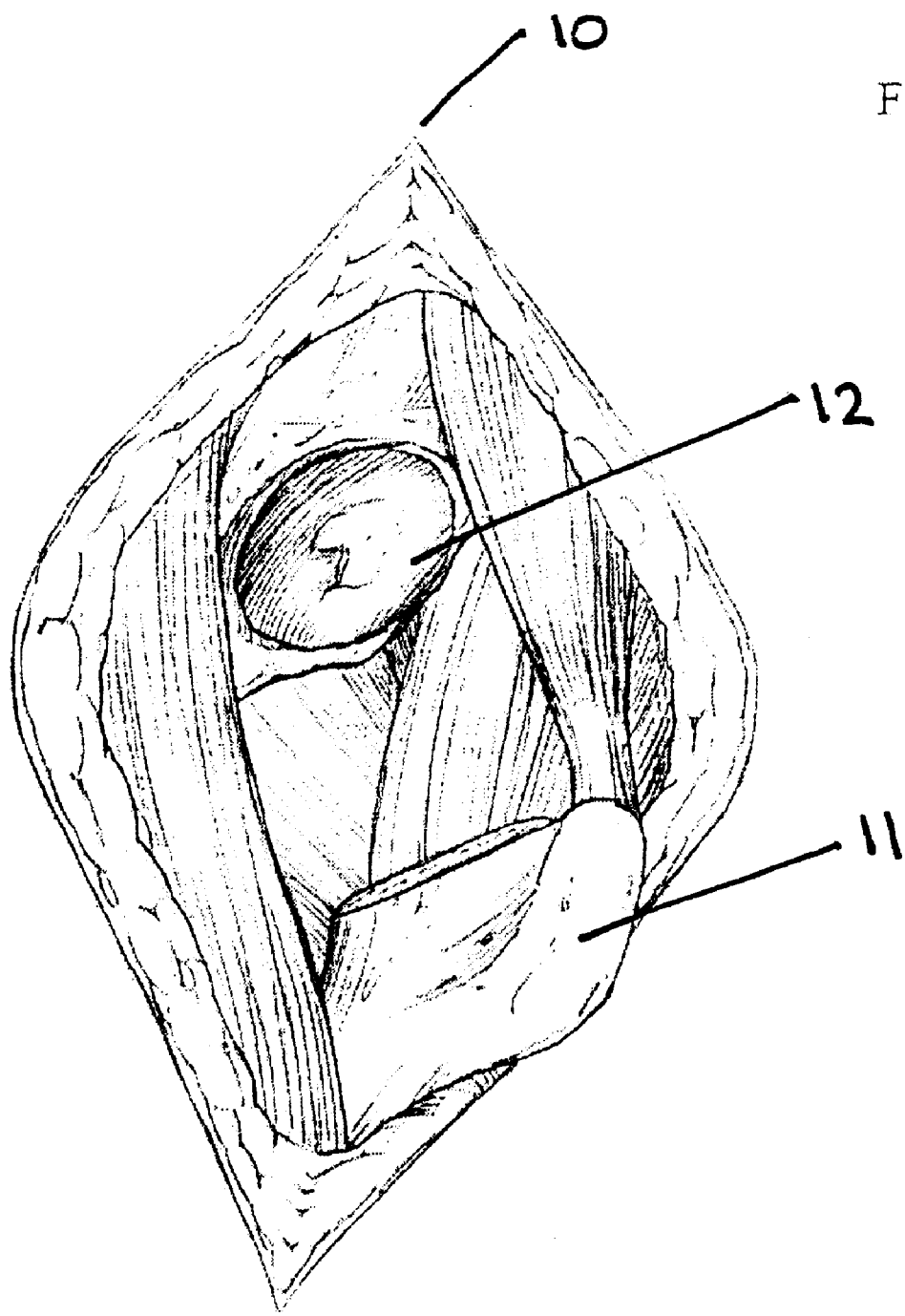
FIG. 1 is an illustration of hip anatomy and conventional exposure for total hip replacement.

FIG. 1 illustrates the general anatomy of the hip joint and a typical surgical approach 10 to the hip joint to expose the proximal femur 11 and the acetabulum 12. In traditional total hip replacement there are generally four surgical approaches to the hip joint. These include posterior approaches without trochanteric osteotomy, trans-trochanteric approaches, anterior approaches without trochanteric osteotomy, and Smith-Peterson approaches. Such approaches are described in detail in various orthopedic reference text such as "Operative Orthopedics," edited by M. W. Chapman, MD, J. B. Lippincott Company, 1988. In addition, a direct lateral approach is commonly used for total hip arthroplasty. The most common surgical approach to the hip is posterior, and the musculature disrupted may include the short internal and external rotators, tensor fascia femoris, quadratus femoris, piriformis, and on occasion part of the gluteus medius and minimus, and the gluteus maximus.

Figure 2:
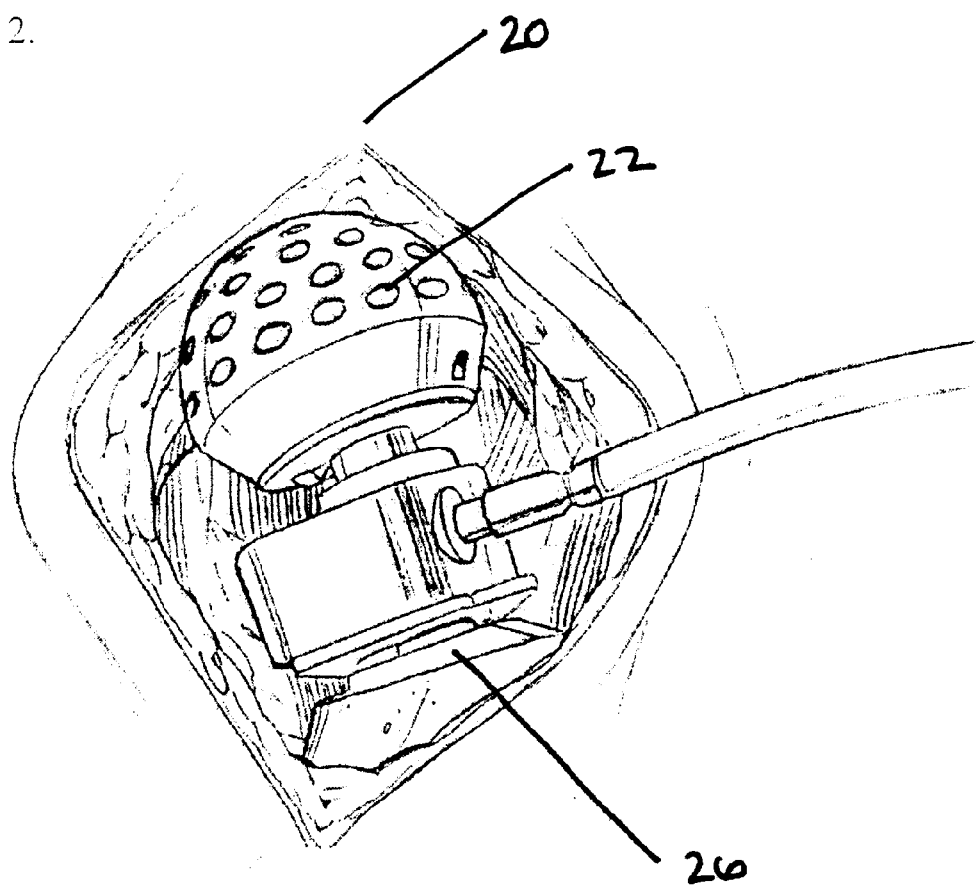
FIG. 2 is an illustration of exposure for minimally invasive total hip replacement with reamer.

In minimally invasive total hip surgery, the incision 20 is typically 6 cm as shown in FIG. 2. While 6 cm, or 2–4 inches, is a typical length for a minimally invasive surgical incision, there may be some variation due to patient physiology, surgeon preferences, and/or other factors. The surgical approach involves separating the gluteus maximus muscle through blunt dissection to gain access to the hip joint capsule and the trochanteric fossa. Muscle disruption is usually limited to release of the piriformis tendon at the trochanteric fossa. It should be noted that there are variations to the surgical approaches described that are known to someone skilled in the art.

FIG. 2 illustrates a minimally invasive surgical approach to the hip joint. The general approach is posterior, and the musculature disrupted includes release of the piriformis tendon. The incision is just large enough to expose the femoral head and acetabulum, and to enable placement of a hemispherical reamer 22, drive mechanism 24, and femoral broach 26.

In contrast to the minimally invasive technique provided, a total hip replacement surgery involves exposing the hip joint through a large incision to provide the surgeon full visualization of the hip joint and the acetabular region and access for surgical power instruments. The femoral head is removed and the femoral canal is reamed and broached to prepare a bony surface to support a hip stem. The stem may be cemented in place, or press fit for bony ingrowth. The acetabulum is prepared, most typically using a hemispherical reamer attached to a surgical hand drill to remove cartilage down to bleeding bone. The surgical exposure as shown in FIG. 1 generally ranges between eight and twelve inches in length and may result in extensive trauma to the soft tissues surrounding the hip joint.

Minimally Invasive Acetabular Reamer System

Figure 3:
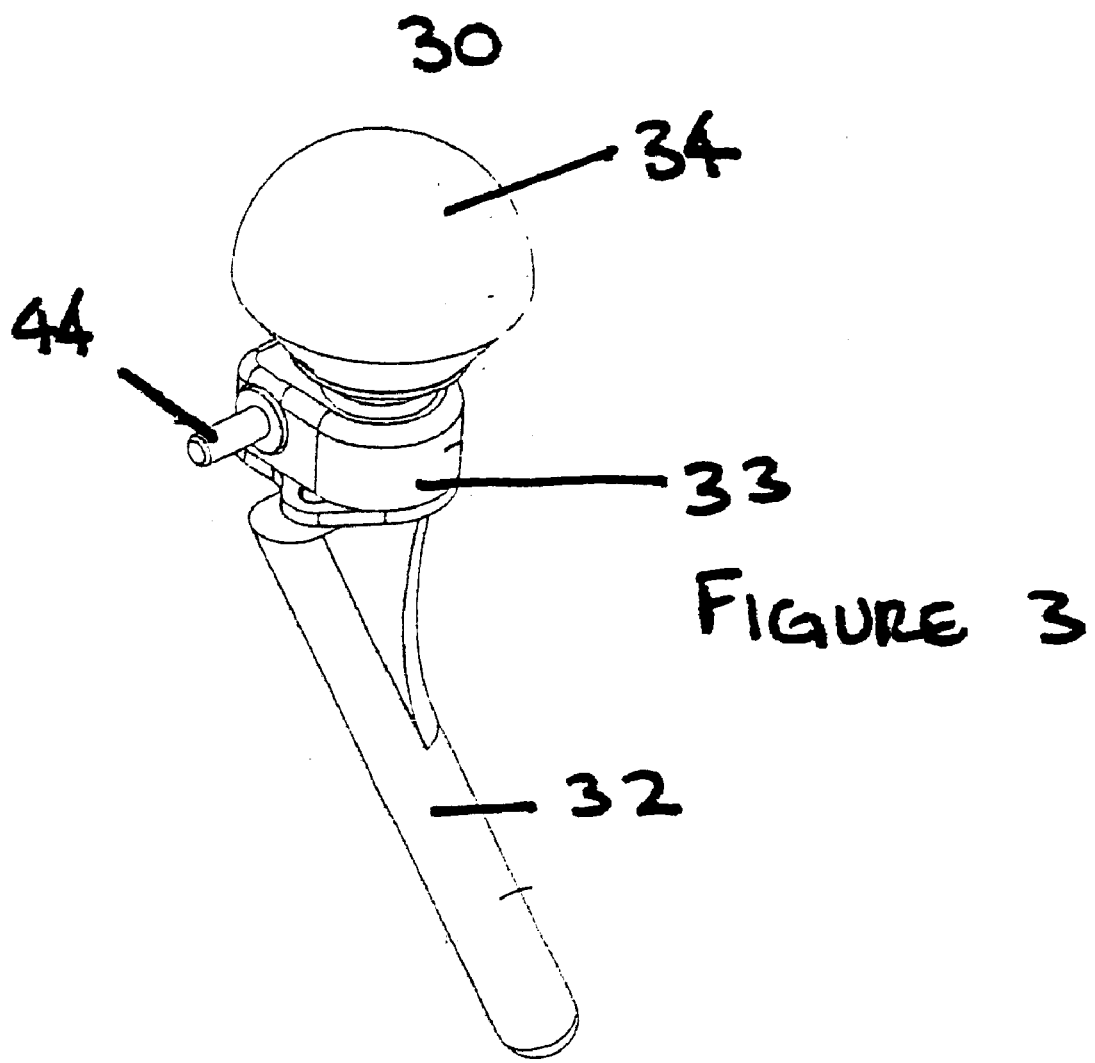
FIG. 3 is an illustration of a minimally invasive acetabular reamer in accordance with one embodiment of the present invention.

As seen in FIG. 3, the MIAR of the present invention, for use with hip replacement surgery, is either a modular or non-modular construct comprising a femoral trial 32, a drive mechanism 33 (either integral or separate) and a hemispherical reamer 34 or similar device for removing cartilage and bone from the acetabular fossa. The hemispherical reamer 34 or similar device includes an attachment component (not shown) for attaching either to the femur, directly or indirectly, or to a mount that itself is attachable to the femur, directly or indirectly. Discussion of the attachment of the MIAR to the femur, directly or indirectly, should be read as broadly encompassing attachment by the reamer directly to the femur (or femoral component) or attachment by the reamer to a mount that is attached to the femur (or femoral component). The reaming system, especially as a modular construct, enables placement of the components through a small incision and minimizes the number of components in the instrument set. In the minimally invasive procedure, the proximal femur does not have to be displaced during acetabular preparation as is necessary with conventional hip arthroplasty. Therefore, the procedure requires only a minimal release of muscles and tendons and, consequently, minimal trauma to muscles and tendons that attach to the proximal femur. Although the invention is described in the context of a total hip replacement, it is understood that the invention has application throughout orthopedics where the surfaces of an articulating joint are to be modified or resurfaced to restore function and relieve pain. The MIAR system uses a drive mechanism anchored to or mounted on a device such as a reamer, broach, or other suitable device that is secured to one bone and, with the joint reduced or placed in position of reduction, may be activated to prepare, with a hemispherical reamer, or suitable bone sculpting tool, the opposite side of the joint to receive artificial components.

With reference to the hip joint, the femoral head is removed either before or after the femoral canal is reamed and broached to prepare a bony surface to support the hip stem or broach to be inserted. The minimally invasive acetabular reamer is mounted to the broach, reamer, trial femoral component or other device inserted into the proximal femur. It is possible to attach the MIAR directly to the proximal femur, however the instruments and the femoral implant provide an advantageous support structure as these instruments, such as rasps, broaches or trials, or the implant conform closely to the prepared bony surface and provides a rigid metal structure to which the MIAR may be mounted. Therefore, in the preferred embodiment, the MIAR is directly or indirectly attached to the femoral broach that is secured within the proximal femoral canal. It is noted that throughout the description rasps, trials, broaches, implants, and stems are used interchangeably in relation to the MIAR system. Additional embodiments include attachment of the MIAR directly to the femur, the femoral trial or the femoral implant. With the MIAR directly or indirectly attached to the femur, the reamer head is placed into the acetabulum. The MIAR is activated to initiate cartilage and bone removal as the femur is positioned. The operating surgeon controls the MIAR by placing and/or moving the leg as necessary to create a spherical reaming of the acetabulum.

The femoral trials are available in an array of sizes to accommodate the size range of the proximal femur. The hemispherical reamers are available in a range of diameters to accommodate the size range of the acetabulum. In the preferred embodiment, the drive mechanism is interchangeable amongst the femoral trails and amongst the hemispherical reamers. An alternate embodiment includes a drive mechanism for each femoral trial, or groups of trials. The trials may be grouped by size, or by right and left. The example given is for the MIAR attached directly or indirectly to a femoral rasp. Similar combinations are possible when the drive mechanism is directly or indirectly attached to a femoral trial or femoral implant.

An example procedure according to the present invention includes the following steps: the appropriate femoral trial is placed into the prepared proximal femur; the drive mechanism is placed onto the proximal aspect of the femoral trial followed by placement of the appropriate sized hemispherical reamer onto the drive mechanism; the hip is reduced and the reaming system is activated to prepare the acetabulum. Of course, if the MIAR is not modular, it is placed as a unit, the hip is reduced, and the reaming system is activated.

Figure 8:
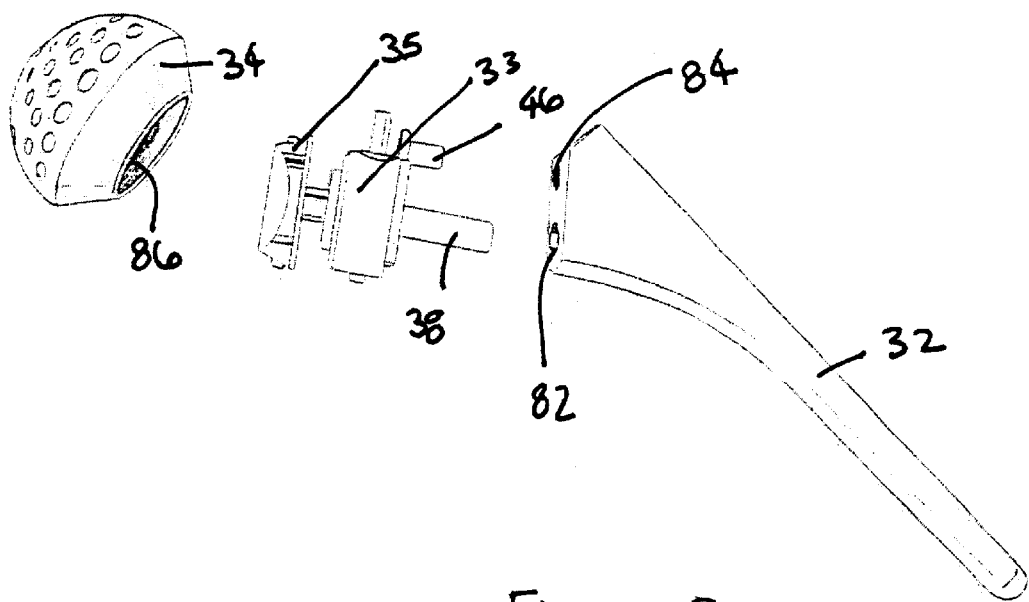
FIG. 8 is an expanded view of a minimally invasive acetabular reamer in accordance with one embodiment of the present invention.

As shown in FIG. 8, the acetabular reamer 34, which is provided in a range of sizes, attaches to the drive mechanism 33 at the support plate 39 that provides quick attachment to the drive mechanism 33. The reamer is preferably rigidly supported on the femoral side such that sufficient stability is provided to prevent relative motion between the MIAR and the femur during articulation. Such stability is generally provided through the placement of the broach 32, femoral trial or femoral implant in the femoral canal. FIG. 3 illustrates an embodiment of a MIAR in accordance with the present invention.

Support for the MIAR is provided by a femoral broach 32. The drive mechanism 33 is supported by the femoral broach 32. FIG. 3 further shows the drive shaft 44 of the drive mechanism 33 supported in the drive mechanism housing, which is supported by the femoral broach 32.

Figure 4:
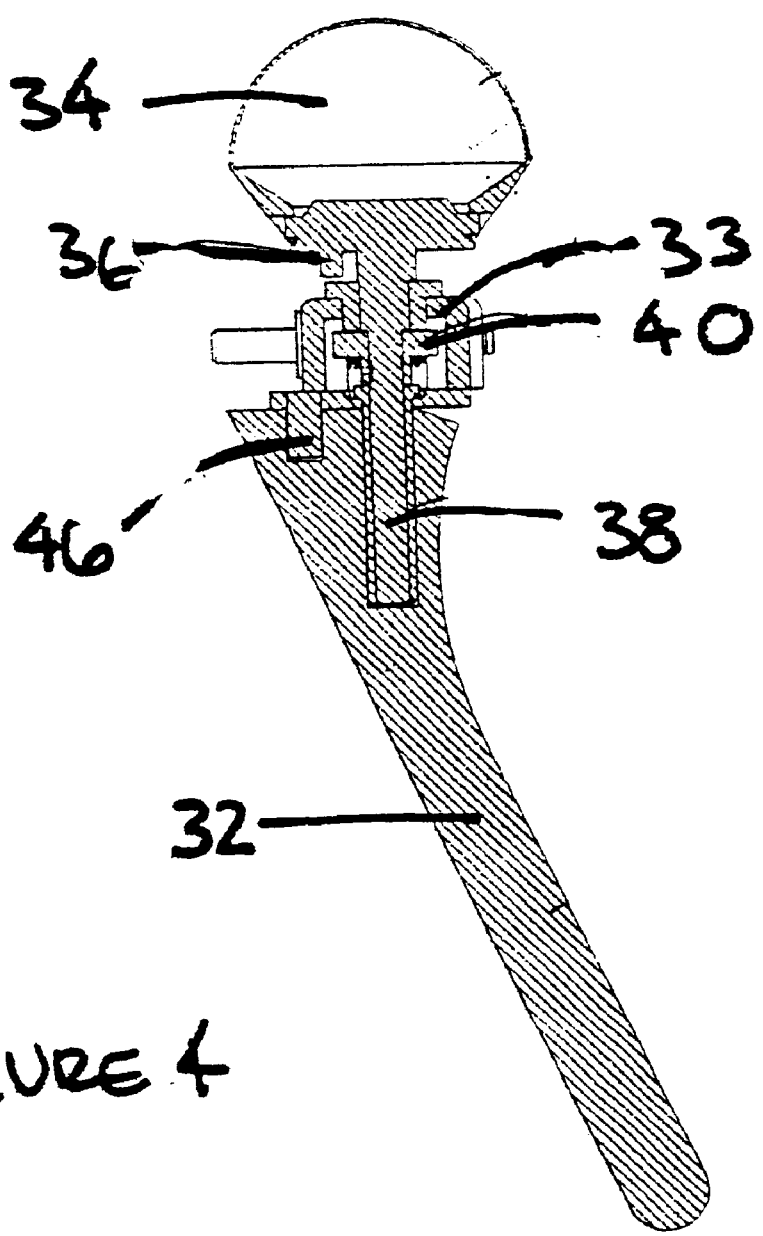
FIG. 4 is a cross sectional view of a minimally invasive acetabular reamer in a sagittal plane in accordance with one embodiment of the present invention.
Figure 5:
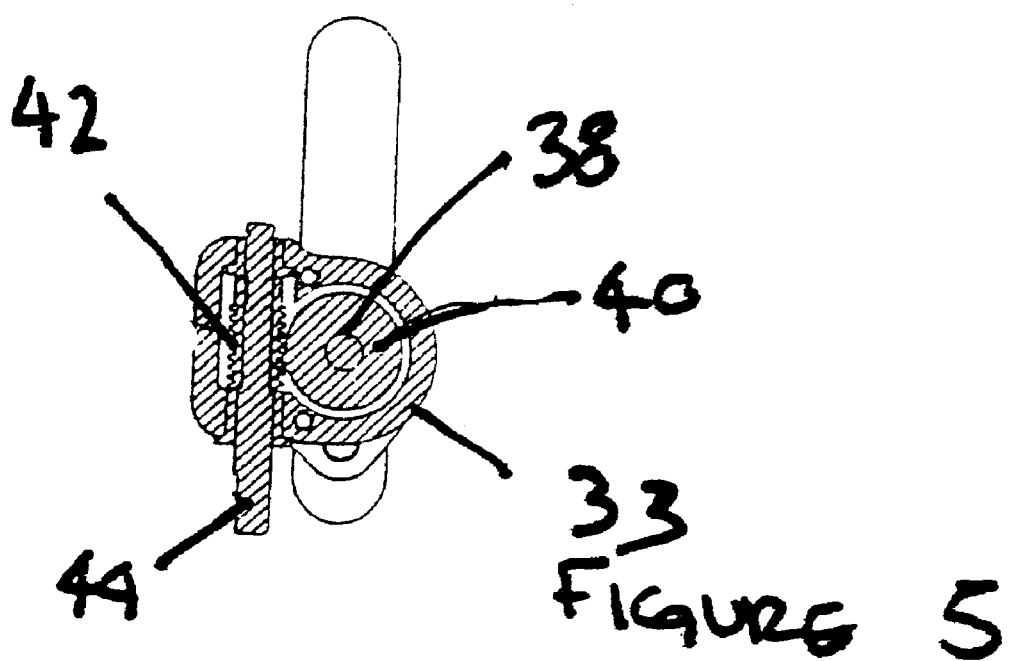
FIG. 5 is a cross sectional view of a minimally invasive acetabular reamer cross in a transverse plane in accordance with one embodiment of the present invention.

As shown in FIG. 5, the drive mechanism 33 may use a worm 42 and worm gear 40 combination, bevel gears, spur gears, belts or chain drives, or other suitable mechanism to transfer rotation or oscillation to the acetabular reamer. In FIG. 4, a worm gear 40 is attached to the drive shaft 38 and in turn is driven by worm (behind worm gear). A worm and worm gear combination represents only one possible drive mechanism that may be used to drive the acetabular reamer and is intended to be illustrative but not limiting. Any other drive mechanism known to those skilled in the art may be used with the present invention. FIG. 5 depicts the worm 42 supported by an input drive shaft 44.

Figure 7:
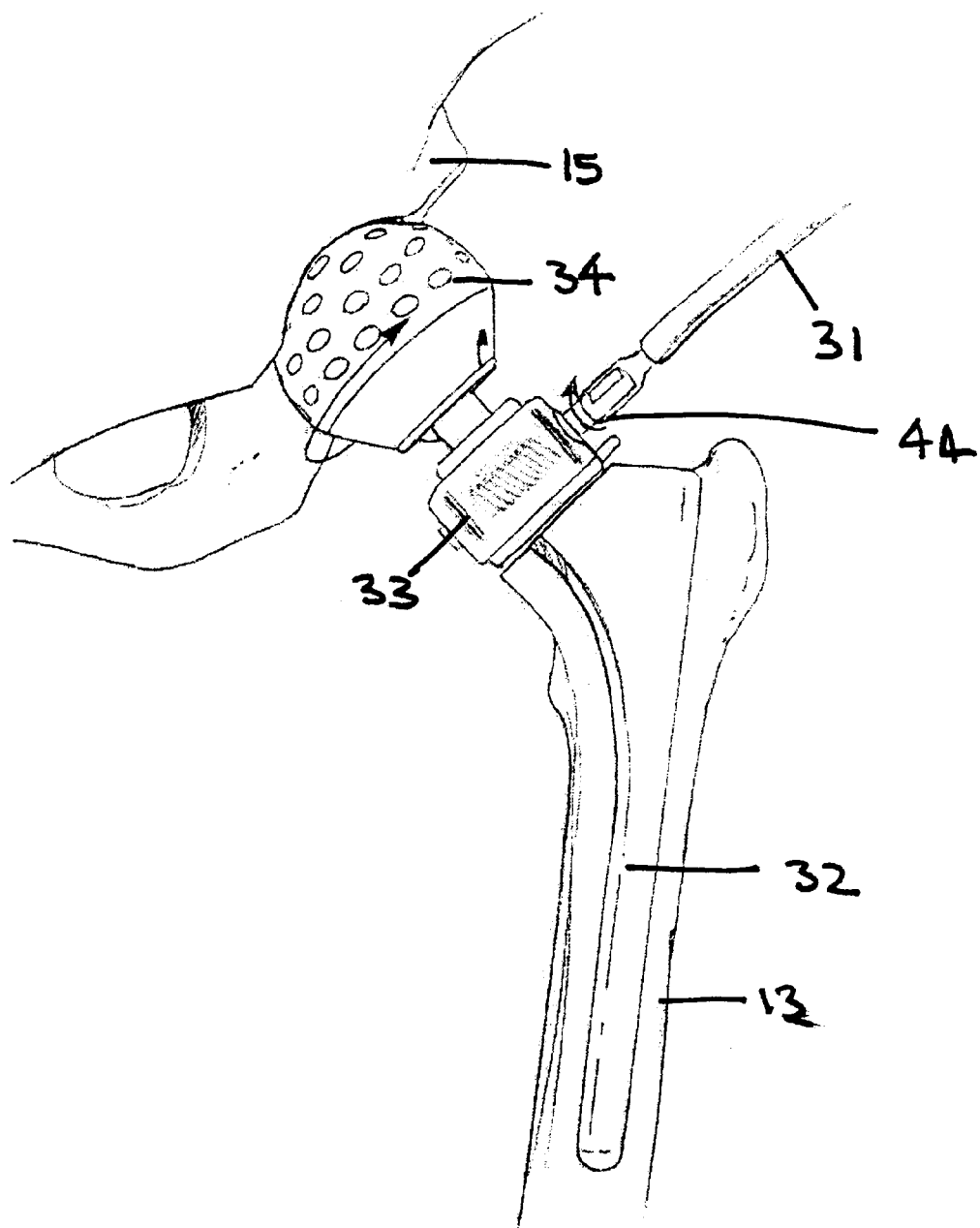
FIG. 7 is an illustration of a minimally invasive acetabular reamer with a worm gear drive mechanism in accordance with yet another embodiment of the present invention.

As shown in FIG. 7, a flexible drive cable 31 is attached to the drive shaft 44. Optionally, a sleeve mounted to the drive mechanism housing may extend through the surgical incision and contain the drive shaft 44 and the flexible cable 31 is attached outside of the surgical incision. Torque generated by the drive mechanism is reacted between the drive mechanism and the femoral trial by a rotational stop 46.

Figure 6:
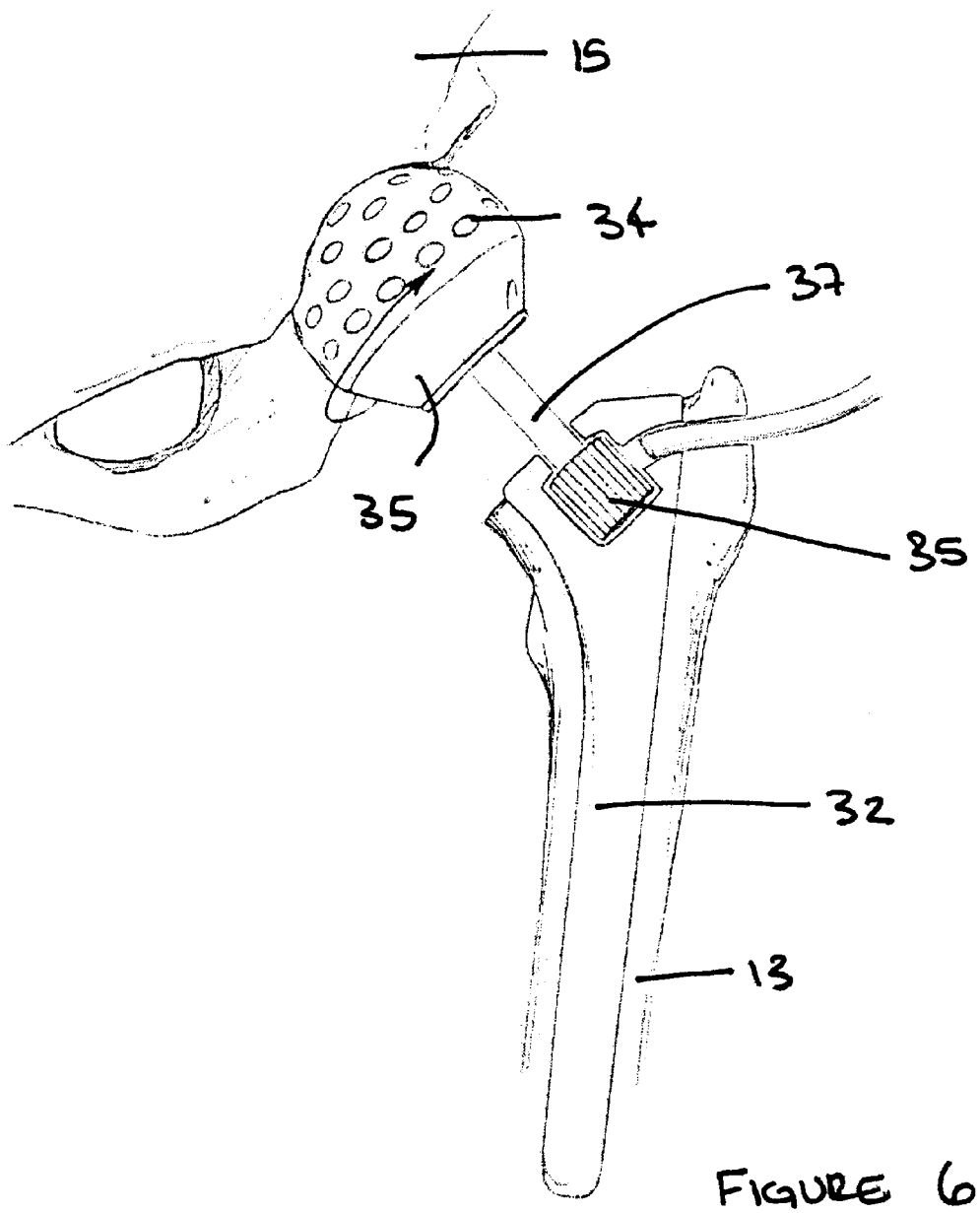
FIG. 6 is an illustration of a minimally invasive acetabular reamer with an integral hydraulic drive in accordance with a further embodiment of the present invention.

The acetabulum is prepared by rotating or oscillating a hemispherical reamer within the acetabulum. Alternatively, non-mechanical cutting instruments such as lasers, water jet cutting, ultrasonic probes, chemical, or other devices to remove tissue can be used. In the current invention, such devices involve rotation or oscillation of the reamer with the device supported by the femur. As shown in FIG. 6, the MIAR may be self-contained with an internal power source to drive the reamer, or may have an external power source to drive the reamer. Likewise, the motor 35 may be internal to the drive mechanism, or may be external with torque transferred to the drive mechanism via appropriate shaft or connection. The drive mechanism may be constructed of mechanical components such as gears, cams, levers, belt and pulleys or chains. The power source may be electrical to drive an electrical motor, fluid to drive a hydraulic motor, gas to drive a pneumatic motor, or any other suitable power source.

Alternatively, the drive mechanism may be configured for use with any one of the attachment mechanisms provided by various manufacturers of total hip systems to attach trial necks to femoral trials. The attachment thus may be a peg in groove, peg in hole, conical taper, a screw fit, or threaded attachment. In a preferred embodiment, the drive mechanism is designed to attach to a femoral trial or rasp/trial provided with the total hip system with which the MIAR is being used. The proximal surface of the drive mechanism is designed with a quick attach mechanism that fits an array of acetabular reamer sizes.

In another embodiment the drive mechanism is supported by the femoral taper that supports the femoral head implant or implant trial. The femoral stem trial is placed into the prepared femoral canal and the appropriate femoral neck trial is placed onto the stem trial. The drive mechanism is placed onto the femoral neck trial taper and the appropriate sized acetabular reamer is directly or indirectly attached to the drive mechanism. Optionally, the femoral stem trial and femoral neck trial may be integrally formed. In this approach, the femoral canal is prepared and the appropriate sized femoral stem is selected based on the patient's femoral anatomy. The femoral stem implant is placed into the prepared femur and the drive mechanism with appropriate sized acetabular reamers is placed onto the implant to prepare the acetabulum.

In alternate embodiments, the drive mechanism may be integral to the femoral trial or the acetabular reamers. The hemispherical reamers are modular and allow changing reamer sizes during the procedure. As seen in FIG. 6, in surgical use, the appropriate femoral broach 32 with integral drive mechanism, in this case a hydraulic motor 35, is placed into the proximal femur and the appropriately sized hemispherical reamer 34 is directly or indirectly attached to the drive mechanism. Alternatively, as seen in FIG. 7, the appropriate acetabular reamer 34 with integral drive mechanism 33 is placed into the acetabular fossa 15 and directly or indirectly attached to the femoral trail 32. Acetabular preparation is performed with the hip joint articulated (reduced).

FIGS. 3, 4, 5, 7 and 8 illustrate the mechanical drive mechanism used in one embodiment of the MIAR system. FIG. 7 shows the MIAR placed into the proximal femur 13 with the hemispherical reamer 34 in contact with the acetabulum 15. FIG. 8 illustrates an exploded view of one embodiment of the MIAR system. The drive shaft 38 extending distally from the drive mechanism 33 passes into receiving hole 82 to attach the drive mechanism 33 to the broach 32. The anti-rotation pin 46 engages receiving hole 84 to add stability and rotational resistance between the drive mechanism and broach. The reamer 34 attaches to a support platform 35 that is part of the drive mechanism 33. The surface 86 of the reamer 34 conically locks to the support platform 35.

FIG. 6 illustrates the MIAR with an internal drive mechanism. A trial broach 32 is placed into the prepared proximal femur 13. The trial stem includes a drive mechanism 35 that is housed within the proximal aspect of the broach 32. The drive mechanism 35, which may be a hydraulic motor, within the broach rotates the drive shaft 37 and support plate 39 which in turn rotates the acetabular 34 reamer to prepare the acetabulum. The acetabular reamer 34 is directly or indirectly attached to the broach via the drive mechanism. Power sources for the drive mechanism to drive the reamer include hydraulic, pneumatic, electric motor (either integral to the femoral trial or via flexible drive cable connecting the motor to the drive mechanism), solenoid or other suitable power source to provide rotation or oscillation to the reamer. Alternately, the drive mechanism may be driven by available surgical power instruments, such as surgical drills, Midas Rex and Anspaq hi speed drill/cutters, etc. Such equipment is available in pneumatic and battery-operated forms. In a preferred embodiment, the drive mechanism is driven by an external power source transferring torque through a flexible drive shaft. Alternatively, the power source may be housed within the femoral trial or broach. The hemispherical acetabular reamers may be reamers, cutters, or other device used for removing cartilage and bone from the acetabular fossa.

In yet another embodiment the acetabular reamer is assembled in a collapsed state to allow ease of reduction of the hip joint with the MIAR system in place. The acetabular reamer is elongated from the femoral housing or from the drive or gear mechanism of the MIAR. This elongation may be accomplished by a variety of devices, for example shim plates, spacers, or other suitable device placed between the elements. Alternatively the MIAR may be elongated by means of pneumatic pressure, lead screw or other power sources. The manner by which the MIAR is elongated is not critical to the invention and any suitable device or method may be used. When sufficient resistance is encountered by the joint capsule and/or other soft tissue elements about the hip, the MIAR is activated to initiate acetabular bone preparation. The process of acetabular reaming is enhanced by pressure created through tensioning the soft tissue elements. In the example of using pneumatic force, gas pressure first elongates the MIAR construct and, after a specified amount of resistance is encountered to elongation, and pneumatic pressure is transferred to elements that generate torque to turn the acetabular reamer.

Figure 9:
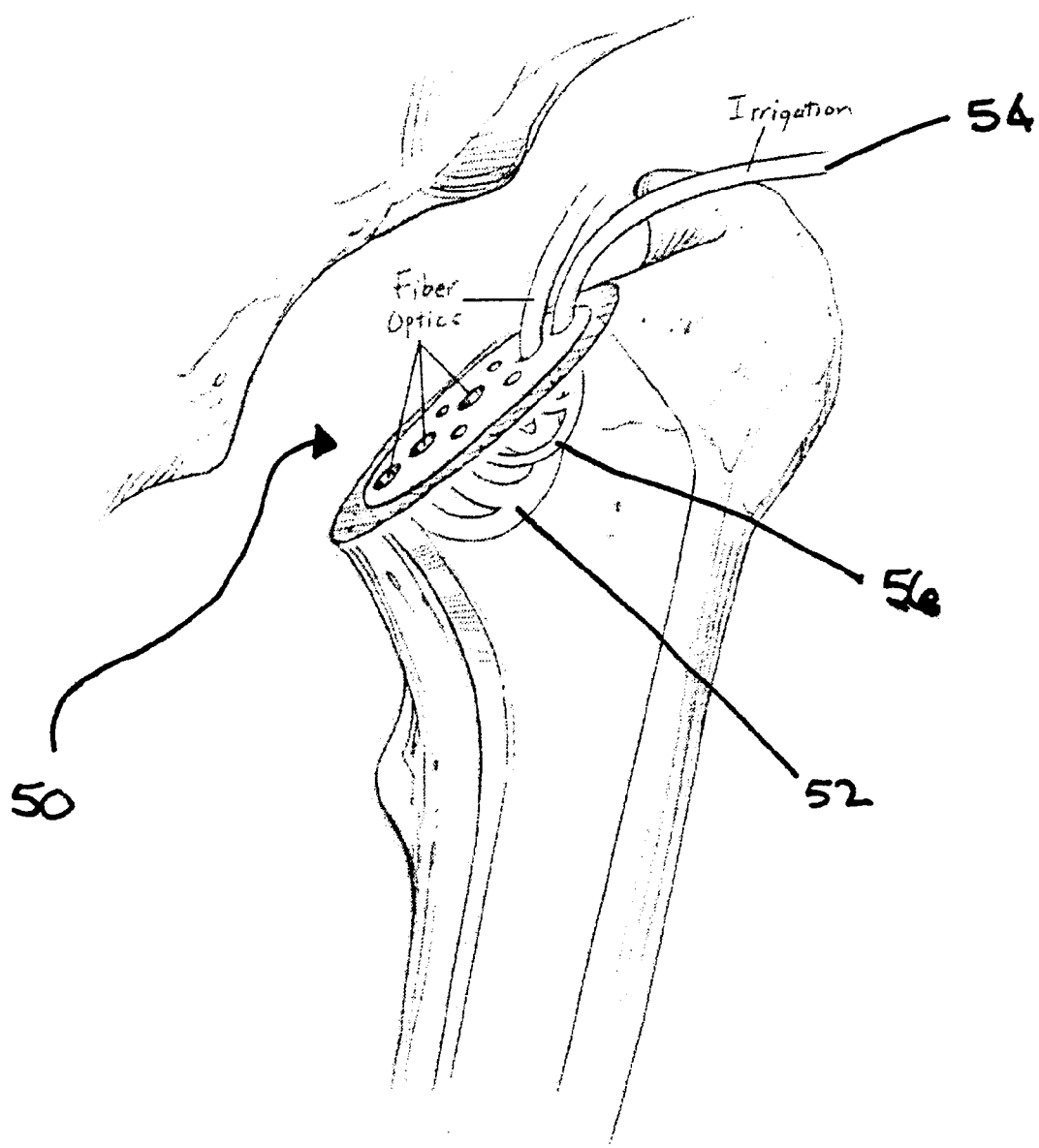
FIG. 9 is an illustration of illumination, visualization, irrigation and suction of an operative site in accordance with one aspect of the present invention.

While minimally invasive techniques are advantageous from a patient rehabilitation perspective, they inherently limit observation of the surgical site. Visualization of the prepared bony surfaces is compromised by the limited access. As seen in FIG. 9, a fiber optic system is provided for inspection of the prepared bony surfaces. The fiber optic system includes a light source (not shown), fiber optic cable 52, imaging base 50 and a digital camera, or other suitable imaging device, and monitoring system to ensure proper preparation of the acetabulum.

Additionally, during a surgical procedure, bone debris and blood will gather in the surgical site and may require periodic removal to enable visualization of the acetabulum. Therefore, an irrigation system and a suction system are provided. Irrigation channels 56 pass through the imaging base 50 and are directed towards the acetabulum. The irrigation and suction systems may be configured as integral to the imaging base 50, or provided as separate instruments available as needed during the procedure.

In practice, the surgeon may periodically stop the reamer and disarticulate the hip joint to view the preparation of the acetabulum. In a preferred embodiment, the imaging base is directly or indirectly attached to the femoral trial, along with the irrigation and suction systems, after the hemispherical reamer and drive mechanism are removed. The imaging base is placed in proximity to the acetabulum by repositioning the femur. The irrigation and suction systems may be used to clear the site of bone debris and blood. The site is illuminated via the fiber optic cable and light source. The digital camera, or other imaging device, images the prepared acetabulum via the fiber optic cable and displays the image on the monitor. Alternatively, if the irrigation and suction systems are separate devices, they are used to clear the site after the imaging base has been placed in proximity to the acetabulum.

Optionally, as seen in FIG. 9, the imaging base may be integral to the base used to house the MIAR. The visualization may be done during acetabular preparation and the imaging base need not be changed for the MIAR femoral part for visualization.

In combination with the imaging and irrigation system, and with the MIAR, a device to apply slight positive pressure to the surgical site may be beneficial in controlling blood loss. Pressure may be generated by creating a sealed space over the incision, then applying a positive pressure within the surgical site.

Minimally Invasive Acetabular Impaction System

Once the acetabulum has been prepared, an acetabular implant is secured to the supporting bone, usually by either bone cement or press-fit. In the case of a cemented acetabular component, the bone surface is oversized relative to the implant size. The bony surface and the implant are covered with bone cement. The implant is then placed into the acetabulum and pressed into position forming a uniform layer of bone cement between the acetabular component and supporting bone. In the case of a press fit acetabular component, the bone surface is line-to-line or slightly undersized relative to the implant size. The implant is impacted into place in the supporting bone. In standard total hip surgery, a straight handled impactor is commonly used to impact the acetabular component. The extensive exposure typically used in traditional total hip surgery provides the clearance to align the impactor relative to the acetabulum. However, in the case of a minimally invasive total hip, the incision is too small to allow proper orientation of a standard straight handled impactor. Use of a standard impactor requires making a second incision to pass the impactor through muscle and tissue in the correct orientation relative to the acetabulum. The acetabular component must be positioned properly to provide normal function and to prevent dislocation of the hip joint. Making a second incision and disrupting more muscle is contrary to the goal of a minimally invasive procedure. Therefore, a device that impacts the acetabular component through a minimally invasive incision is needed. In one embodiment, the current invention includes a device designed to directly or indirectly attach to the femoral trial and provide an impaction force to properly seat the implant. A variety of acetabular components and methods for placement thereof may be used. Example components for implanting in the acetabulum include, but are not limited to, cemented shells or press fit cups.

Figure 10:
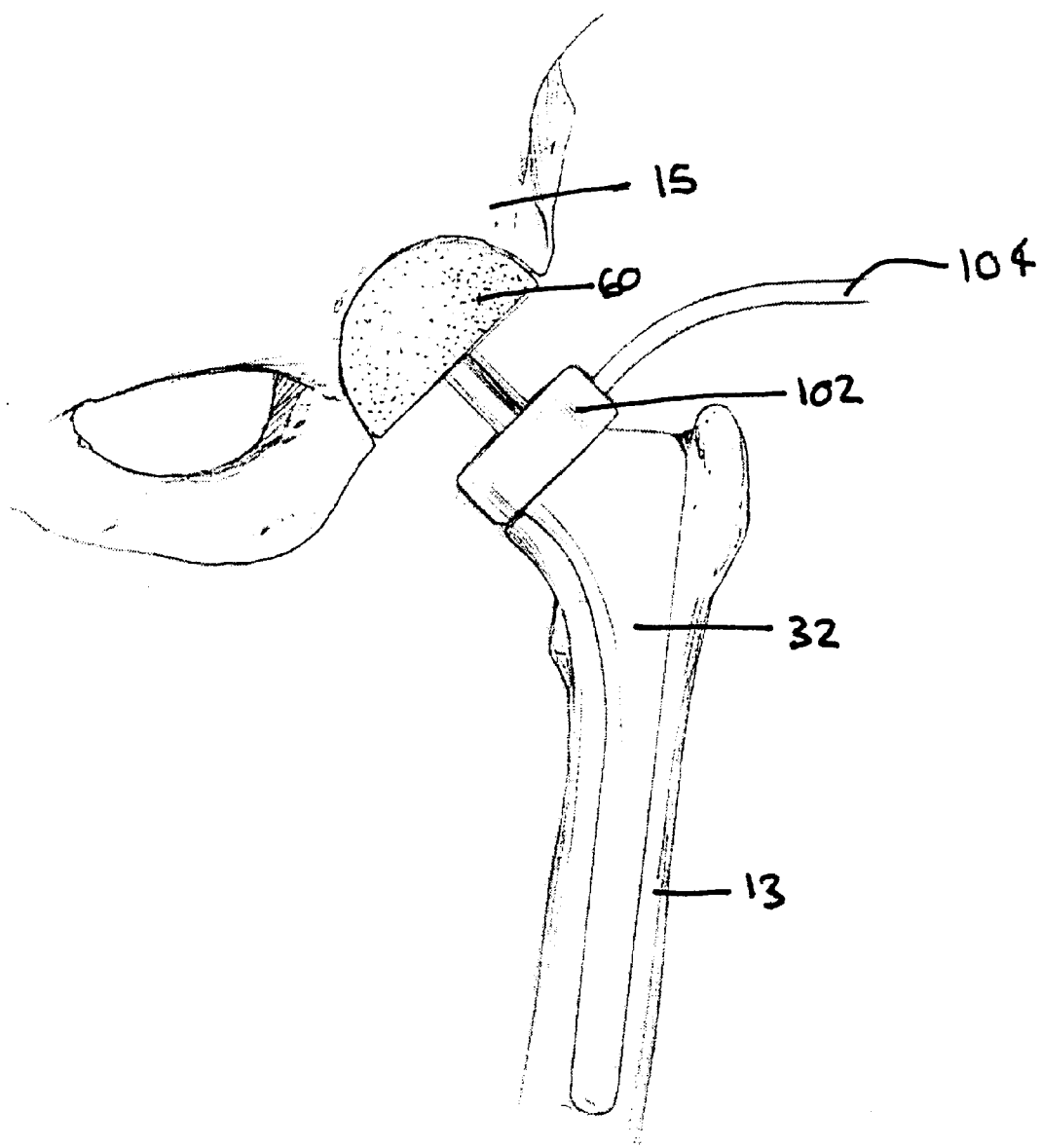
FIG. 10 is an illustration of a minimally invasive impaction system in accordance with one embodiment of the present invention.

As seen in FIG. 10, the impaction device preferably includes a pneumatic impaction hammer 102 mountable to the femoral broach 32 and an optional attachment component for attaching to the shell 60 of the acetabular component. The impaction device 102 and acetabular component 60 may be placed into the surgical site independently and assembled in the operative site. Alternatively, the impaction device 102 and acetabular component 60 may be assembled prior to placing the impaction device onto the broach 32. With the acetabular shell directly or indirectly attached to the impactor, and the impactor secured to the femoral broach, the shell is placed into the acetabulum by reducing the hip joint. The broach, femur and mass of the leg serve as counter weights to counteract the force of the impaction device. An additional counter weight may be directly or indirectly attached to the impaction device via a connection shaft extending out of the incision and attaching to a weight or external resistance to impaction forces.

Figure 11:
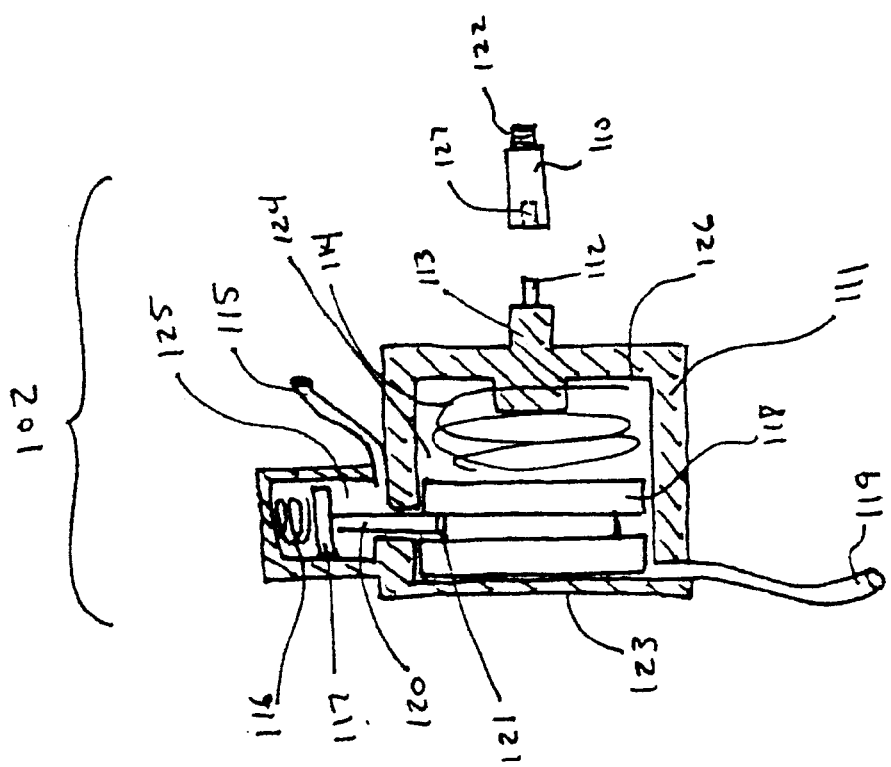
FIG. 11 is a detailed depiction of a minimally invasive impactor in accordance with one embodiment of the present invention.

The impaction device may be powered by a pneumatic impaction hammer, a hydraulic piston, a linear actuator or solenoid, an electromechanical device, a spring activated device, or any other suitable force generating mechanism. The power source may originate outside of the operative site, or may be integral with the impaction device. As an alternative a hand held impactor with a handle angled to allow access through a minimally invasive incision may be used to impact the acetabular component. In a preferred embodiment, the impactor is a single ended air driven piston and cylinder as show in FIG. 11. The back face 123 of the impactor housing 111 is configured to attach to the broach previously described. Within the housing is a primary piston 118 that travels in a primary cylinder 124. In its retracted position (shown) a push rod 120 of a secondary piston 117 engages a retaining groove 121 in a primary piston 118. The secondary piston 117 is held in an extended position by a secondary spring 116. Air pressure is applied via a primary tube 119 to the back of the primary piston 118 to charge system. The primary piston 118 is held in place by the push rod 120 of the secondary piston 117. Air pressure is applied to the secondary tube 115 to pull the push rod and the secondary piston 117 out of the retaining groove 121 in the primary piston 118, thereby releasing the primary piston 118 to impact the top surface of the cylinder 126. The impaction force is carried through the impactor housing 111 and delivered to the acetabular shell (not shown) via a cup adaptor 110. The cup adaptor 110 has a threaded end 122 that engages the acetabular shell. The other end of the cup adaptor 110 has a box shaped recess 127 that fits over a mating prominence 112 on the top surface of the impactor housing 111.

After an impaction cycle the pressure to the primary tube 119 is released and the primary piston 118 is forced back into a retracted position by a return spring 114. When the primary piston 118 is in its retracted position the air pressure to the secondary tube 115 is released and the secondary piston 117 is pushed back into locked position by a secondary return spring 116. Pressure is reapplied to the primary tube 119 to charge the impactor and the cycle is repeated.

In surgical use, the cup impactor 102 and broach may be assembled outside of the surgical site, then placed into the prepared proximal femur. Alternatively, the broach may first be placed into the proximal femur, then the cup impactor 102 attached to the broach. With the cup impactor 102 in place, the cup adaptor 110 is attached to the cup implant and the recess 127 in the adapter is placed over the mating prominence 112 on the top of the cup impactor. The hip joint is reduced, placing the acetabular shell into the acetabulum. An alignment guide (not shown) is attached to the cup impactor to aid the surgeon in properly orientating the shell with respect to the pelvis. Alternatively, a surgical navigation system may be used to position the acetabular shell by referencing the cup impactor and the acetabulum. Once in position, the shell is impacted into the acetabulum by triggering the cup impactor with successive impactions. In a preferred embodiment the trigger releases one impaction, then the cup impactor resets for a further impaction, as necessary. In an alternate embodiment the trigger releases continuous impactions for the duration the trigger is on.

Or course the impaction device is suitable for use in placing an implant other than an acetabular component. The impaction device may be used for seating an implant in a second bone in any joint replacement wherein the implant may be placed on the impaction device, aligned with a second bone, and force imparted to the implant, the force being reacted with the first bone and the second bone.

A Typical Surgical Procedure for the MIAR is as Follows

Using the instrumentation shown, the articular surface of the acetabulum may be sculpted according to the patient's individual physiology by articulating the femur with reference to the acetabulum. The method involves providing an apparatus having a bone sculpting tool directly or indirectly attached to a bone mount, such as a femoral trial stem, attaching the mount rigidly to the femur with the tool in bone sculpting engagement with the acetabulum, and then sculpting the acetabulum by articulating the femur with respect to the joint.

The hip joint is a ball in socket joint, hence rotation of the femur while supporting the MIAR will result in a spherical preparation of the acetabulum. Alternatively, the MIAR, having a suitable reamer and drive mechanism, may be placed into the acetabulum to remove bone without rotating the femur.

In a preferred embodiment, the trochanteric fossa is surgically accessed with a minimal disruption of muscle and tendon insertions to the trochanter and surrounding area. The approach may be at the posterior border of the gluteus medius and minimus, anterior in the interval between sartorius and rectus, or a direct lateral exposure. The hip may be dislocated posteriorly if a posterior approach is used or anteriorly if either a lateral or anterior approach is used. Alternatively, the hip may remain reduced while the femoral canal is prepared and the femoral neck is resected.

The femoral neck is resected and the femoral head is removed. The resection and removal may be performed with conventional cutting devices such as oscillating saws. The femur is oriented to align the femoral canal with the incision. The femoral canal is prepared using sequential reaming and broaching. Bony preparation is per the technique specified for the particular total hip stem being used and at the surgeon's discretion.

An appropriately sized femoral trial is placed into the femur. The drive mechanism is directly or indirectly attached to the femoral trial. Preferably, the drive mechanism is designed to mount directly onto the femoral trial.

The acetabular reamer is directly or indirectly attached to the drive mechanism. The appropriate acetabular reamer is selected by the surgeon. The surgeon may choose to measure the diameter of the removed femoral head as an aid in selecting the most appropriately sized acetabular reamer.

The hip joint is reduced and the hip is articulated with the drive mechanism and acetabular reamer in place. Elongation of the MIAR construct is optionally carried out to appropriately tension the soft tissue elements about the hip. The drive mechanism is activated to prepare the acetabulum. If necessary, the femur may be advanced while the hip joint is manipulated to ensure spherical and uniform reaming of the acetabulum. Imaging may be used to check the orientation and depth of the acetabular reamer.

At the surgeon's discretion, depth of reaming and uniformity of reaming may be checked periodically during the procedure. This may be done by dislocating the hip, removing the reamer and attaching the illumination and irrigation devices (or a combined illumination and irrigation device) to the femoral trial. The hip is reduced with the illumination and irrigating devices in place and the operative site is cleared with irrigation and suction. The prepared surface of the acetabulum may then be inspected. After inspection, the illumination and irrigation devices are removed and the drive mechanism and reamer are replaced. Alternatively, depth of reaming may be assessed under fluoroscopic imaging of the hip joint.

The articulation of the hip joint to prepare the acetabulum may be repeated with sequentially larger reamers until the appropriate size is reached. Further, the size and preparation may be checked with the illumination and irrigation devices as necessary. Once the appropriate size is reached, the acetabular reamer and the drive mechanism are removed.

After preparation of the acetabulum, an appropriate acetabular component is implanted. The appropriate acetabular component may be pre-selected or may be selected after surgical preparation of the acetabulum. If the desired component is a cemented cup, the cup is cemented in place.

If the desired component is a press fit cup, a cup impactor is attached to the broach and placed into the prepared proximal femur. Alternatively, the broach may be place in the prepared femoral canal first and then attach the cup impactor to the broach. The acetabular shell is attached to the cup adaptor and placed onto cup impactor. The hip joint is reduced and the shell is positioned in the acetabular fossa. An alignment guide is attached to the cup impactor to aid the surgeon in proper orientation of the shell during impaction. The cup impactor is triggered, thereby impacting the shell. An alternative technique for placing a press fit cup may use image guided surgery or an alignment device protruding from the incision. The guiding system is used to advance the cup into proper orientation. The MIAI impactor is activated to securely seat the cup into the acetabulum. Regardless of technique, after placement of the press fit cup, the impaction device is removed. Alternatively, a surgical navigation system may be used for positioning, aligning, and monitoring the cup or cup impactor during impaction. Cup monitoring includes real time evaluation of the cup position relative to anatomical landmarks captured by the surgical navigation system after preparing the acetabulum and before placing the cup so as to indicate cup seating and cup alignment.

The acetabular liner is placed into the shell and a trial femoral neck and head are placed onto the femoral trial. The range of motion and hip stability are checked and the appropriate femoral implant is selected. The femoral trials are removed and the femoral component is implanted per manufacturer specifications.

Additional steps as known to those skilled in the art may be performed within the scope of the invention. Further, one or more of the listed steps need not be performed in a procedure within the scope of the present invention.

What is claimed is:

1. An apparatus for sculpting the articular surface of a second bone that normally articulates with a first bone, the apparatus comprising:
   a bone sculpting tool including an attachment portion for attaching the bone sculpting tool to the first bone in a position for sculpting the articular surface of the second bone.

2. The apparatus of claim 1, further comprising a mount for attachment to the attachment portion, the mount being adapted for attachment to the femur.

3. The apparatus of claim 1, wherein the bone sculpting tool is configured for attachment to a femur in a position for sculpting the articular surface of an acetabulum.

4. The apparatus of claim 3, wherein the attachment portion is adapted for direct attachment to the femur.

5. The apparatus of claim 3, wherein the attachment portion is adapted for indirect attachment to the femur.

6. The apparatus of claim 5, wherein the attachment portion is adapted for attachment to a femoral trial.

7. The apparatus of claim 5, wherein the attachment portion is adapted for attachment to a femoral broach.

8. The apparatus of claim 5, wherein the attachment portion is adapted for attachment to a femoral stem.

9. The apparatus of claim 3, wherein the bone sculpting tool is designed for rotation.

10. The apparatus of claim 3, wherein the bone sculpting tool is designed for oscillation.

11. The apparatus of claim 3, wherein the bone sculpting tool comprises a hemispherical reamer.

12. The apparatus of claim 3, further including a drive mechanism for driving the bone sculpting tool.

13. The apparatus of claim 12, wherein the drive mechanism is integral to a mount.

14. The apparatus of claim 12, wherein the drive mechanism is integral to a femoral trial.

15. The apparatus of claim 12, wherein the drive mechanism is configured for attachment to a femoral stem.

16. The apparatus of claim 3, wherein the bone sculpting tool is adapted for elongation.

17. The apparatus of claim 16, wherein the bone sculpting tool has an axis of rotation, and the elongation is along the axis of rotation.

18. The apparatus of claim 16, further including a lead screw for elongation of the bone sculpting tool.

19. The apparatus of claim 16, further including shims for elongation of the bone sculpting tool.

20. The apparatus of claim 16, further including a pneumatic powered device for elongation of the bone sculpting tool.

21. The apparatus of claim 12, wherein the drive mechanism comprises a gearbox.

22. The apparatus of claim 12, wherein the drive mechanism comprises a worm and worm gear combination.

23. The apparatus of claim 12, wherein the drive mechanism comprises a bevel gear combination.

24. The apparatus of claim 12, wherein the drive mechanism includes a motor.

25. The apparatus of claim 12, further including a flexible drive shaft for connecting the drive mechanism to a motor.

26. The apparatus of claim 24, wherein the motor is a surgical power drill.

27. A method of sculpting the articular surface of a second bone that normally articulates with a first bone in a joint, the method comprising the steps of:
   providing a bone sculpting tool;
   attaching the bone sculpting tool to the first bone in a position for sculpting the articular surface of the second bone;
   aligning the bone sculpting tool with the second bone; and
   sculpting the articular surface of the second bone by engaging the bone sculpting tool with the articular surface of the second bone.

28. The method of claim 27, wherein the step of attaching the bone sculpting tool to the first bone includes attaching the bone sculpting tool to a mount and attaching the mount to the first bone.

29. The method of claim 27, wherein the step of attaching the bone sculpting tool to the first bone includes attaching the bone sculpting tool directly to the first bone.

30. The method of claim 27, wherein the step of attaching the bone sculpting tool to the first bone includes attaching the bone sculpting tool indirectly to the first bone.

31. The method of claim 27, wherein:
   the step of attaching the bone sculpting tool to the first bone comprises attaching the bone sculpting tool to a femur;
   the step of aligning the bone sculpting tool with the second bone comprises placing the bone sculpting tool in the acetabulum; and
   the step of sculpting the articular surface of the second bone by engaging the articular surface of the second bone comprises sculpting the articular surface of the acetabulum by engaging the articular surface of the acetabulum.

32. The method of claim 31, wherein the step of attaching the bone sculpting tool to the femur includes attaching the bone sculpting tool directly to the femur.

33. The method of claim 31, wherein the step of attaching the bone sculpting tool to the femur includes attaching the bone sculpting tool indirectly to the femur.

34. The method of claim 33, wherein the step of attaching the bone sculpting tool to the femur comprises the steps of attaching the bone sculpting tool to a femoral trial and placing the femoral trial in the femur.

35. The method of claim 33, wherein the step of attaching the bone sculpting tool to the femur comprises the steps of attaching the bone sculpting tool to a broach and placing the broach in the femur.

36. The method of claim 33, wherein the step of attaching the bone sculpting tool to the femur comprises the steps of attaching the bone sculpting tool to a femoral implant and implanting the femoral implant in the femur.

37. The method of claim 31, further including the steps of elongating the bone sculpting tool to engage the acetabulum and tensioning soft tissue structures spanning the joint.

38. The method of claim 31, further including the step of retracting the bone sculpting tool to ease the step of placing the bone sculpting tool within the acetabulum.

39. A system for minimally invasive sculpting and replacing the articular surface of a second bone that normally articulates with a first bone, the system comprising:
   a bone-sculpting apparatus comprising a bone-sculpting tool including a tool attachment portion for attaching the bone sculpting tool to the first bone in a position for sculpting the articular surface of the second bone; and
   an impaction apparatus for providing force between the first bone and the second bone, the impaction apparatus comprising an impaction device including an impaction attachment portion for attaching the impaction device to the first bone.

40. The system of claim 39, wherein the impaction apparatus further comprises an adapter for mounting the implant.

41. The system of claim 39, wherein further including a visualization apparatus, irrigation apparatus, and a suction apparatus all configured as a single device.

42. The system of claim 39, further comprising a visualization apparatus comprising a light source, an imaging base, an imaging device, and a display.

43. The system of claim 41, wherein the visualization apparatus further includes a monitoring system.

44. The system of claim 42, wherein the imaging base is integral to a mount configured for attachment to the attachment portion of the bone sculpting apparatus, the mount being attachable to the first bone.

45. The system of claim 42, further including an irrigation apparatus integral to the imaging base.

46. The system of claim 42, further including a suction apparatus integral to the imaging base.

47. The system of claim 42, further including an irrigation apparatus and a suction apparatus integral to the imaging base.

48. The system of claim 39, further including an irrigation apparatus.

49. The system of claim 39, further including a suction apparatus.

50. The system of claim 39, further including a surgical navigation system for positioning, aligning and monitoring the implant.

51. The system of claim 39, further including a surgical navigation system for positioning, aligning and monitoring the impaction device.

52. A method of sculpting, in a surgical site, the articular surface of a second bone that normally articulates with a first bone, the method comprising the steps of:
   providing a bone sculpting tool;
   attaching the bone sculpting tool to the first bone;
   aligning the bone sculpting tool with the second bone and sculpting the articular surface of the second bone by engaging the bone sculpting tool with the articular surface of the second bone;
   providing an implant;
   providing an impaction apparatus comprising an impaction device configured for attachment to the first bone;
   attaching the impaction apparatus to the first bone;
   placing the implant on the impaction apparatus and imparting force to the implant to secure the implant to the second bone, the force being reacted by the second bone and the first bone.

53. The method of claim 52, further including a monitoring device including a visualization apparatus, an irrigation apparatus, and a suction apparatus.

54. The method of claim 52, further comprising the steps of providing a visualization apparatus comprising a light source, an imaging base, an imaging device, and a display system and visualizing the surgical site with the visualization apparatus.

55. The method of claim 52, further comprising the steps of providing an irrigation apparatus and a suction apparatus and clearing the surgical site of bone debris and blood using the irrigation apparatus and the suction apparatus.

56. The method of claim 52, further comprising the step of clearing the site of bone debris and blood using the irrigation apparatus and the suction apparatus.

57. The method of claim 52, further comprising the steps of positioning, aligning and monitoring the implant with a surgical navigation system.

58. The method of claim 52, further comprising the steps positioning, aligning and monitoring the impaction device with a surgical navigation system.

59. The method of claim 52, wherein:
   the step of attaching the bone sculpting tool to the first bone comprises attaching the bone sculpting tool to a femur;
   the step of aligning the bone sculpting tool with the second bone and sculpting the articular surface of the second bone comprises placing the bone sculpting tool within an acetabulum and sculpting articular surface of the acetabulum;
   the step of attaching the impaction apparatus mount to the first bone comprises attaching the impaction apparatus mount to a femur;
   and the step of imparting force to the implant comprises imparting force to an acetabular shell for securing the acetabular shell to the acetabulum, the force being reacted by the acetabulum and the femur.

* * * * *